United States Patent
Wu et al.

(10) Patent No.: US 11,624,746 B2
(45) Date of Patent: Apr. 11, 2023

(54) TEST STRIP FOR MILK IMMUNOFLUORESCENCE ASSAY (IFA) AND USE THEREOF

(71) Applicant: Hangzhou Fudemin Biotechnology Co., Ltd., Hangzhou (CN)

(72) Inventors: Yong Wu, Hangzhou (CN); Xin Li, Hangzhou (CN); Xuanyi Meng, Hangzhou (CN); Ping Tong, Hangzhou (CN); Juanli Yuan, Hangzhou (CN); Ying Feng, Hangzhou (CN)

(73) Assignee: Hangzhou Fudemin Biotechnology Co., Ltd., Hangzhou (CN)

( * ) Notice: Subject to any disclaimer, the term of this patent is extended or adjusted under 35 U.S.C. 154(b) by 152 days.

(21) Appl. No.: 17/201,884

(22) Filed: Mar. 15, 2021

(65) Prior Publication Data
US 2022/0146506 A1    May 12, 2022

(30) Foreign Application Priority Data
Nov. 10, 2020  (CN) .......................... 202011243428.0

(51) Int. Cl.
*G01N 33/543*    (2006.01)
(52) U.S. Cl.
CPC .  *G01N 33/54386* (2013.01); *G01N 33/54346* (2013.01); *G01N 33/54388* (2021.08); *G01N 2800/24* (2013.01)
(58) Field of Classification Search
CPC ......... G01N 2800/24; G01N 33/54388; G01N 33/53
See application file for complete search history.

(56) References Cited

FOREIGN PATENT DOCUMENTS

| CN | 104267189 A | * | 1/2015 | ............. | G01N 33/68 |
| CN | 111896749 A | * | 11/2020 | | |

OTHER PUBLICATIONS

Cai et al, CN103267189A Claim translation, Nov. 6, 2020, CNIPA (Year: 2020).*
Liu et al., CN 104267189A Claim translation, Jan. 7, 2015, CNIPA (Year: 2015).*

(Continued)

*Primary Examiner* — Jennifer Wecker
*Assistant Examiner* — Mickey Huang
(74) *Attorney, Agent, or Firm* — Dorsey & Whitney LLP

(57) ABSTRACT

The present disclosure provides a test strip for milk immunofluorescence assay (IFA) and use thereof, and relates to the technical field of test strip. The test strip of the present disclosure includes a sample pad, a conjugate pad, a nitrocellulose membrane, and a wicking pad assembled and pasted successively on a PVC backing card; fluorescent latex microsphere-labeled mixed antibodies are coated on the conjugate pad; anti-casein antibody (T1 line), anti-beta-lactoglobulin (BLG) antibody (T2 line), anti-alpha-lactalbumin (ALA) antibody (T3 line), anti-lactoferrin/anti-bovine serum albumin (BSA) antibody (T4 line), and rabbit anti-mouse IgG antibody (C line) are coated on the nitrocellulose membrane, where the T1, T2, T3, and T4 lines are test lines, and the C line is a control line. The test strip of the present disclosure accurately and quantitatively detects the content of casein, BLG, ALA, and lactoferrin/BSA in food, and features easy operation and high accuracy and sensitivity.

20 Claims, 1 Drawing Sheet

(56) References Cited

OTHER PUBLICATIONS

Masiri et al., Development and Validation of a Lateral Flow Immunoassay Test Kit for Dual Detection of Casein and beta-Lactoglobulin Residues, Journal of Food Protection, 2016, vol. 79, 477-483 (Year: 2016).*

Anfossi et al., Multiplex Lateral Flow Immunoassay: An Overview of Strategies towards High-throughput Point-of-Need Testing, 2018, biosensors, (Year: 2018).*

* cited by examiner

TEST STRIP FOR MILK IMMUNOFLUORESCENCE ASSAY (IFA) AND USE THEREOF

TECHNICAL FIELD

The present disclosure relates to the technical field of the test strip, and in particular to a test strip for milk immunofluorescence assay (IFA) and use thereof.

BACKGROUND

Food allergen refers to an antigenic substance present in food, capable of selectively activating human cells, inducing a specific antibody response and causing allergic reactions. In general, food allergens are proteins or glycoproteins having a molecular weight of 10,000-70,000. Common allergenic foodstuffs include milk, beans, eggs, cereals, tree nuts, shellfish, and so on. Among factors threatening the human health indicated in a World Health Organization (WHO) report, food allergy ranks fourth. In recent food-related warning notifications inside and outside of China, the number of allergen issues ranks second, which is next only to microbial contamination and becomes a globally concerned industry focus. Food allergen issues have different understanding and concern extent in different countries and regions. Food allergens have been widely reported and investigated and even specifically legislated in developed countries. For example, Directive 2003/89/EC of the European Parliament and of the Council supervises foodstuff production and distributors, and Directive 2006/142/EC of the European Parliament and of the Council lists 14 food allergens which must clearly appear on the labeling of foodstuffs. In the USA, milk, eggs, fish, Crustacean shellfish, tree nuts, wheat, peanuts, and soybeans are listed as major allergens that require mandatory labeling in the Food Allergen Labeling and Consumer Protection Act of 2004.

There are big gaps between China and developed countries in studies of food allergens and levels of concern thereon, and food allergen issue is the major issue that China's food export enterprises are notified by foreign parties. So far, the management of food allergen labeling is still in the infancy in China. The earliest management standard relevant to food allergen labeling is the Food Safety for Beijing Olympic Games—Food Allergens Labeling issued during the 2008 Beijing Olympic Games, which was abolished after the Olympic Games. In 2009, in order to reinforce the management of food allergens, China issued a voluntary national standard GB/T 23779-2009 Allergenic Ingredients in Prepackaged Foods, where allergen is defined and eight major groups of voluntarily labeled food allergens are listed. In 2012, GB 7718-2011 National Food Safety Standard General Rules for Nutrition Labeling of Prepackaged Foods was issued, and officially the food allergen labeling issue fell under label management for the first time; however, the general rules have not specifically regulated how to label allergens, and thus consumers do not pay enough attention to allergic reactions caused thereby. As the Chinese Government carries out food safety efforts and in a deep-going way and promotes the development of food import and export trade, it is more and more important to perfect the management of food allergen labeling.

Among the eight major foods or food groups, milk is the main nutritional source for infants, young children and even adults; however, patients with milk allergy will suffer from gastrointestinal discomfort due to drinking milk, and children's health and development will be influenced. Patients with milk allergy occupy a considerable proportion of those with food allergy (about 2% in adults and about 6% in children). Moreover, milk contains casein, beta-lactoglobulin, alpha-lactalbumin, and other components, where allergy sufferers may be allergic to one or all of these components. It follows that it is very important to detect what milk components the allergy sufferers are allergic to and indicate what allergens are identified in milk. So far, milk detection methods principally include enzyme-linked immunosorbent assay (ELISA) and Western blot (WB), which require long reaction time and complex operation, are susceptible to changes in enzyme activity, and obtain less accurate results.

SUMMARY

In view of this, an objective of the present disclosure is to provide a test strip for milk IFA and use thereof; the test strip for IFA enables rapid quantitative detection of milk allergens, featuring easy operation, high accuracy and sensitivity.

To achieve the above purpose, the present disclosure provides the following technical solutions.

The present disclosure provides a test strip for milk IFA, where the test strip includes a sample pad, a conjugate pad, a nitrocellulose membrane, and a wicking pad arranged successively on a polyvinyl chloride (PVC) backing card in a left-to-right and end-to-end manner; fluorescent latex microsphere-labeled mixed antibodies are coated on the conjugate pad; the mixed antibodies include: anti-casein antibody, anti-beta-lactoglobulin (BLG) antibody, anti-alpha-lactalbumin (ALA) antibody, anti-lactoferrin/anti-bovine scrum albumin (BSA) antibody;

the nitrocellulose membrane includes four test lines and one control line in parallel; the test lines are coated with the anti-casein antibody, the anti-BLG antibody, the anti-ALA antibody, and the anti-lactoferrin/anti-BSA antibody, respectively; the antibodies coated on the test lines and the fluorescent latex microsphere-labeled mixed antibodies present an antibody pair.

Preferably, the fluorescent latex microsphere is 50-500 nm in particle size.

Preferably, a method for preparing the fluorescent latex microsphere includes a step of adsorbing fluorescence labeled streptavidin with latex microspheres; where a fluorescence marker includes fluorescein isothiocyanate, rhodamine B, tetramethyl rhodamine isothiocyanate (TRITC), or fluorescein CY5.

Preferably, in the mixed antibodies, the anti-casein antibody, the anti-BLG antibody, the anti-ALA antibody, and the anti-lactoferrin/anti-BSA antibody have a mass ratio of 1:1:1:1.

Preferably, in the anti-lactoferrin/anti-BSA antibody, the anti-lactoferrin antibody and the anti-BSA antibody have a mass ratio of (0.8-1.2):1.

Preferably, the mixed antibodies coated on the conjugate pad have a concentration of 2-10 µL/cm.

Preferably, the rabbit anti-mouse IgG antibody coated on the control line has a coating concentration of 0.5-5 µL/em.

The present disclosure further provides use of the test strip for IFA in the detection of milk allergens.

Preferably, milk allergic components include casein, BLG, ALA, lactoferrin and/or BSA.

The present disclosure provides a test strip for milk IFA, having a structure as shown in FIG. 1; a sample pad, a conjugate pad, a nitrocellulose (NC) membrane, and a wicking pad are assembled and pasted successively on a PVC hacking card. Herein, fluorescent latex microsphere-labeled mixed antibodies including anti-casein antibody, anti-BLG antibody, anti-ALA antibody, anti-lactoferrin/anti-BSA antibody are coated on the conjugate pad; the anti-casein antibody (T1 line), the anti-BLG antibody (T2 line), the anti-ALA antibody (T3 line), the anti-lactoferrin/BSA antibody (T4 line), and rabbit anti-mouse IgG antibody (C line) are coated on the NC membrane successively, where the T1, T2, T3, and T4 lines are test lines, and the C line is a control line. The test strip of the present disclosure accurately and quantitatively detects the content of casein, BLG, ALA, and lactoferrin/BSA in food, and features easy operation and high accuracy; recovery rate shall be 90%-110%, with high sensitivity (≤0.84 ng/mL).

DETAILED DESCRIPTION

The present disclosure provides a test strip for milk IFA, where the test strip includes a sample pad, a conjugate pad, a nitrocellulose membrane, and a wicking pad arranged successively on a PVC hacking card in a left-to-right and end-to-end manner; fluorescent latex microsphere-labeled mixed antibodies are coated on the conjugate pad; the mixed antibodies include: anti-casein antibody, anti-BLG antibody, anti-ALA antibody, anti-lactoferrin/anti-BSA antibody;

the nitrocellulose membrane includes four test lines and one control line in parallel; the test lines are coated with the anti-casein antibody, the anti-BLG antibody, the anti-ALA antibody, and the anti-lactoferrin/anti-BSA antibody, respectively; the antibodies coated on the test lines and the fluorescent latex microsphere-labeled mixed antibodies present an antibody pair.

Figure 1:
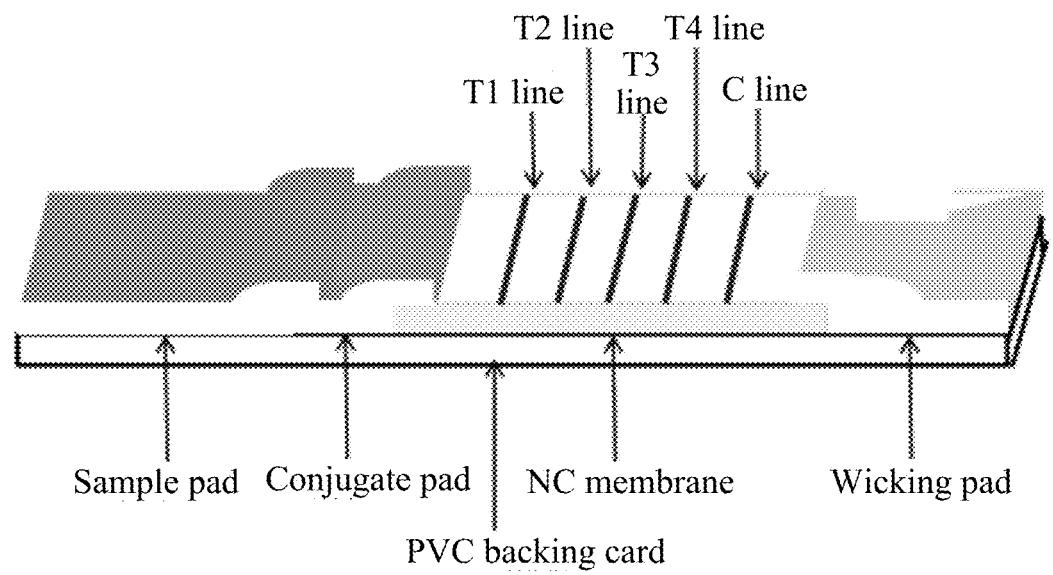
FIG. 1 illustrates the structure of the test strip for IFA provided by the present disclosure.

The test strip for IFA provided by the present disclosure has a structure as shown in FIG. 1; a sample pad, a conjugate pad, a nitrocellulose (NC) membrane, and a wicking pad are assembled and pasted successively on a PVC hacking card. The fluorescent latex microsphere-labeled mixed antibodies are coated on the conjugate pad of the present disclosure. The fluorescent latex microspheres may preferably be 50-500 nm in particle size. A method for preparing the fluorescent latex microsphere of the present disclosure may include a step of adsorbing fluorescence labeled streptavidin with latex microspheres; a fluorescence marker may include fluorescein isothiocyanate, rhodamine B, tetramethyl rhodamine isothiocyanate (TRITC), or fluorescein CY5.

A method for preparing the conjugate pad of the present disclosure may preferably include the steps of:

(a) adsorptively binding fluorescence-labeled streptavidin to latex microspheres to obtain fluorescent latex microspheres;

(b) binding biotin to the mixed antibodies to obtain biotinylated mixed antibodies;

(c) mixing the fluorescent latex microspheres with the biotinylated mixed antibodies to obtain fluorescent latex microsphere-labeled mixed antibodies; and (d) spraying the fluorescent latex microsphere-labeled mixed antibodies on a conjugate pad. There is no temporal relation between steps (a) and (b).

In the present disclosure, the fluorescence-labeled streptavidin and the latex microspheres may preferably have a mass ratio of 1:40 in step (a); in step (b), the biotin and the mixed antibodies may preferably have a volume ratio of 1:4; in step (c), the fluorescent latex microspheres and the biotinylated mixed antibodies may preferably have a volume ratio of 10:1. In the mixed antibodies of the present disclosure, the anti-casein antibody, the anti-BLG antibody, the anti-ALA antibody, and the anti-lactoferrin/anti-BSA antibody have a mass ratio of 1:1:1:1. Sources of all antibodies in the mixed antibodies are not particularly limited in the present disclosure, as long as commercially available antibodies may preferably be selected. The anti-lactoferrin/anti-BSA antibody of the present disclosure may preferably include anti-lactoferrin antibody and anti-BSA antibody, and the anti-lactoferrin antibody and the anti-BSA antibody may preferably have a mass ratio of 1:1. In step (d) of the present disclosure, the fluorescent latex microsphere-labeled mixed antibodies may preferably be sprayed on the conjugate pad in an amount of 2-10 μL/cm. In the present disclosure, all of the fluorescent latex microsphere-labeled mixed antibodies may be detection antibodies.

The NC membrane includes four test lines and one control line in parallel; the test lines are coated with the anti-casein antibody (T1 line), the anti-BLG antibody (T2 line), the anti-ALA antibody (T3 line), and the anti-lactoferrin/anti-BSA antibody (T4 line), respectively; the control line may preferably be coated with the rabbit anti-mouse IgG antibody (C line, coating concentration 0.5-5 μL/cm). The antibodies coated on the test lines of the NC membrane of the present disclosure are equivalent to capture antibodies and paired with the above-mixed antibodies (detection antibodies), respectively.

Methods for preparing the NC membrane are not particularly limited in the present disclosure, preferably including steps of: diluting the mixed antibodies of the anti-casein antibody, the anti-BLG antibody, the anti-ALA antibody, and the anti-lactoferrin/anti-BSA antibody, and the rabbit anti-mouse IgG antibody with coating buffer, respectively; streaking five diluted antibodies on the NC membrane in parallel, respectively; after permeation of the antibodies into the NC membrane, forming a test zone coated with the anti-casein antibody, the anti-BLG antibody, the anti-ALA antibody, and the anti-lactoferrin/anti-BSA antibody and a control zone coated with the rabbit anti-mouse IgG antibody, respectively. In the present disclosure, when streaking the test zone, diluted antibodies may preferably be streaked at a concentration of 3 mg/mL (liquid output of peristaltic pump 0.4 mL/min, streaking speed 50 m/20 min) and blast-dried in a drying oven at 20° C. for 12 h. When streaking the control zone, the diluted antibody may preferably be streaked on the NC membrane at a concentration of 5 mg/mL (liquid output of peristaltic pump 0.4 mL/min. streaking speed 50 m/20 min); the line is parallel to the lines in the test zone and blast-dried in the drying oven at 20° C. for 12 h. In the present disclosure, after the streaking, further, the NC membrane may preferably be blocked with blocking buffer for 60 min at 37° C., removed, dried for 2 h at 37° C. and sealed in a bag for use.

Preferably, in the present disclosure, the sample pad, the conjugate pad, the NC membrane, and the wicking pad may be assembled and pasted on the PVC backing card, and cut into test strips as shown in FIG. 1 on a slitter as required (4 mm).

The present disclosure further provides use of the above test strip for IFA in the detection of milk allergens.

In the present disclosure, the milk allergens may preferably include casein, BLG, ALA, lactoferrin and/or BSA.

The present disclosure further provides a method for detecting milk allergens using the above test strip for IFA, preferably including steps of: dropping 100-120 μL of test sample onto a sample pad, placing a test strip on a specific fluorescence microplate reader 15 min after the completion of reaction in a control zone, and reading fluorescence signal intensity for quantitative determination. In the present disclosure, after the test sample is dropped onto the sample pad, the sample reacts with and binds to the mixed antibodies on the conjugate pad, reacts with the anti-casein antibody, the anti-BLG antibody, the anti-ALA antibody, and the anti-lactoferrin/anti-BSA antibody in a test zone successively, and finally reaches a control zone to end the reactions.

The test strip for milk IFA and the use thereof provided by the present disclosure will be described in detail below in conjunction with examples, but they should not be construed as limiting the protection scope of the present disclosure.

Example 1

1. Preparation of Conjugate Pad

1) Preparation of fluorescent latex microspheres: Adsorption buffer (50 mM, pH 5.8 citrate buffer) was used to dilute latex microspheres with a particle size of 400 nm to obtain 6 mL of latex microsphere suspension with a final concentration of 30 mg/mL; red fluorescein rhodamine-labeled streptavidin was charged into the adsorption buffer in a volume ratio of 1:(50-500), with a final volume of 6 mL; the above latex microsphere suspension was charged into the above adsorption buffer with red fluorescein rhodamine-labeled streptavidin to obtain a mixture; the resulting mixture was incubated for 1-2 h at room temperature while constantly stirring, followed by centrifugation; a precipitate was collected, dissolved in storage buffer (adsorption buffer with 0.06% BSA), and stored at 4° C. for use.

2) Preparation of Biotinylated Mixed Antibodies

Anti-casein antibody (Abeam Cat #ab166596, Gene Tex Cat #GTX37769), anti-BLG antibody (Abeam Cat #ab229780, Gene Tex Cat #GTX42670), anti-ALA (Abeam Cat #ab112972, Cloud-clone Corp. Wuhan, Cat #PAB018Mu01), and anti-lactoferrin/anti-BSA antibody [a 1:1 mixture of Anti-Lactoferrin Antibody (Cat #ab112968) and Anti-Bovine Serum Albumin Antibody [1C12] (Cat #ab79827)] were mixed in an equal ratio to obtain mixed antibodies; the mixed antibodies were diluted to 3 mL with 0.2 M pH 4.7 sodium acetate buffer, and the mixed antibodies were fully dialyzed with 0.2 M pH 4.7 sodium acetate buffer alternatively; 1 mL of N-hydroxysuccinimidohiotin (NHSB) was dissolved in 1 mL of dimethyl sulfoxide (DMSO) to obtain an NHSB solution; 25 µL of NHSB was charged into the above 3 mL of mixed antibodies, stirred for 2-4 h, continuously stirred for 10 min at room temperature, and dialyzed with 20 mM, pH 3.9 phosphate buffer saline (PBS) to obtain biotinylated mixed antibodies.

3) Preparation of Fluorescent Latex Microsphere-Labeled Milk Antibody

The fluorescent latex microspheres obtained in step 1) and the biotinylated mixed antibodies obtained in step 2) were mixed in a ratio of 10:1, and centrifuged after reacting for 30 min; a precipitate was dissolved in storage buffer, followed by restoring the original volume.

4) The Fluorescent Latex Microsphere-Labeled Anti-Milk Mixed Antibodies were Sprayed on the conjugate pad in an amount of 2 µL/cm.

2. Preparation of NC Membrane

1) Membrane treatment: An NC membrane was marked and immersed in pH membrane treatment buffer (TBS) for 5-10 min.

2) Assembly of the sample applicator; an immersed NC membrane was placed on a lay-flat pad, and an antibody application plate was arranged, leaving room for labeling thereon.

3) Preparation of anti-milk antibody test zone: the anti-casein antibody, the anti-BLG antibody, the anti-ALA antibody, and the anti-lactoferrin/anti-BSA antibody were streaked successively at a concentration of 3 mg/mL (liquid output of peristaltic pump 0.4 mL/min, streaking speed 50 m/20 min) and blast-dried in a drying oven at 20° C. for 12 h.

4) Preparation of control zone: the rabbit anti-mouse IgG antibody was streaked on the NC membrane at a concentration of 8 mg/mL (liquid output of peristaltic pump 0.4 mL/min, streaking speed 50 m/20 min); the line was parallel to lines in the test zone and blast-dried in the drying oven at 20° C. for 12 h.

5) The NC membrane was blocked with blocking buffer (prepared from 100 mL of PBS and 0.5 g of BSA) for 60 min at 37° C., removed, dried for 2 h at 37° C., and sealed in a bag for use.

3. Assembly of the Test Strip

A sample pad, a conjugate pad, an NC membrane, and a wicking pad were assembled and pasted on a PVC backing card, and cut into test strips as shown in FIG. 1 on a slitter as required (4 mm).

4. Detection of Antigen to be Tested

After 100-120 µL of test sample was dropped onto the sample pad, the sample reacted with and bound to the anti-milk mixed antibodies on the conjugate pad, reacted with the anti-casein antibody, the anti-BLG antibody, the anti-ALA antibody, and the anti-lactoferrin/anti-BSA antibody in the test zone successively, and finally reached the control zone to end the reactions; the test strip was placed on a specific fluorescence microplate reader, and fluorescence signal intensity was read for quantitative determination.

The linearity of dose-response curve: Serial calibration solutions prepared from a calibrator in a kit were determined; concentrations were 100.00, 50.00, 17.50, 3.50, and 0.35 IU/mL, respectively, and fitted in a double logarithmic model or other appropriate mathematical models. The model fitting result should be consistent with the following: inter-run precision (CV %) should be ≤10.0%; between-run precision (CV %) should be ≤15.0%.

Figure 2:
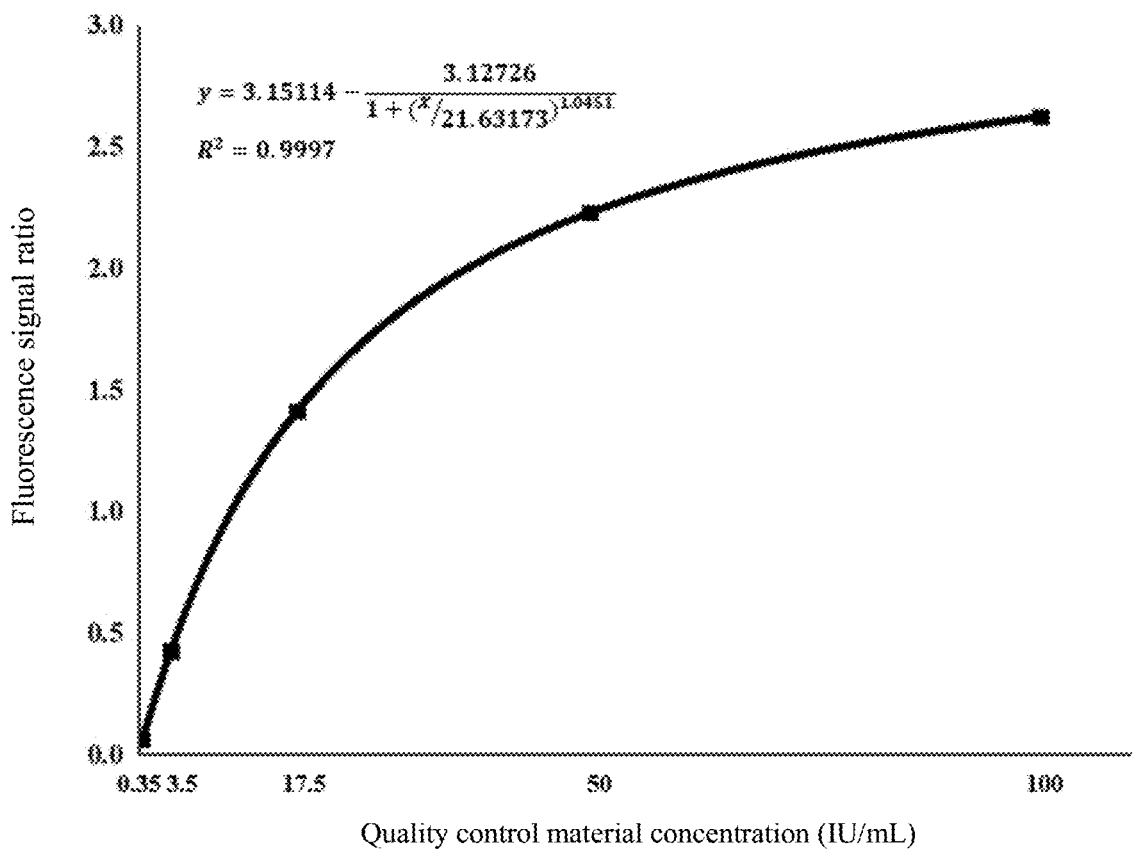
FIG. 2 illustrates a standard curve for IFA.

The linear analysis of the dose-response curve concluded that: within the range of 0.35-100 IU/mL, there was a smooth increasing curve of each concentration versus measured value, and the lower limit of detection (a minimum concentration detected by a test system with CV<15%) was 0.35 IU/mL. The curve equation is shown in FIG. 2:

$$y = 3.15114 - \frac{3.12726}{1 + (x/21.63173)^{1.0451}}, R^2 = 0.9997.$$

The foregoing description is merely a preferred example of the present disclosure; it should be noted that several improvements and modifications can also be made by those of ordinary skill in the art without departing from the principles of the present disclosure, and these improvements and modifications should also be regarded as the protection scope of the present disclosure.

What is claimed is:

1. A test strip for milk immunofluorescence assay (IFA), wherein the test strip comprises a sample pad, a conjugate pad, a nitrocellulose membrane, and a wicking pad arranged successively on a polyvinyl chloride (PVC) backing card in a left-to-right and end-to-end manner; fluorescent latex microsphere-labeled mixed antibodies are coated on the conjugate pad; the mixed antibodies comprise: anti-casein antibody, anti-beta-lactoglobulin (BLG) antibody, anti-alpha-lactalbumin (ALA) antibody, anti-lactoferrin/anti-bovine serum albumin (BSA) antibody;

the nitrocellulose membrane comprises four test lines and one control line in parallel; the test lines are coated with the anti-casein antibody, the anti-BLG antibody, the anti-ALA antibody, and the anti-lactoferrin/anti-BSA antibody, respectively; the antibodies coated on the test lines and the fluorescent latex microsphere-labeled mixed antibodies present an antibody pair.

2. The test strip for IFA according to claim 1, wherein the fluorescent latex microsphere is 50-500 nm in particle size.

3. The test strip for IFA according to claim 2, wherein a method for preparing the fluorescent latex microsphere comprises a step of adsorbing fluorescence labeled streptavidin with latex microspheres; wherein a fluorescence marker comprises fluorescein isothiocyanate, rhodamine B, tetramethyl rhodamine isothiocyanate (TRITC), or fluorescein CY5.

4. The test strip for IFA according to claim 1, wherein in the mixed antibodies, the anti-casein antibody, the anti-BLG antibody, the anti-ALA antibody, and the anti-lactoferrin/anti-BSA antibody have a mass ratio of 1:1:1:1.

5. The test strip for IFA according to claim 1, wherein in the anti-lactoferrin/anti-BSA antibody, the anti-lactoferrin antibody and the anti-BSA antibody have a mass ratio of (0.8-1.2):1.

6. The test strip for IFA according to claim 4, wherein in the anti-lactoferrin/anti-BSA antibody, the anti-lactoferrin antibody and the anti-BSA antibody have a mass ratio of (0.8-1.2):1.

7. The test strip for IFA according to claim 4, wherein the mixed antibodies coated on the conjugate pad have a concentration of 2-10 μL/cm.

8. The test strip for IFA according to claim 1, wherein the control line has a rabbit anti-mouse IgG antibody coated thereon and has a coating concentration of 0.5-5 μL/cm.

9. Use of the test strip for IFA according to claim 1 in the detection of milk allergens.

10. Use of the test strip for IFA according to claim 2 in the detection of milk allergens.

11. Use of the test strip for IFA according to claim 3 in the detection of milk allergens.

12. Use of the test strip for IFA according to claim 4 in the detection of milk allergens.

13. Use of the test strip for IFA according to claim 5 in the detection of milk allergens.

14. Use of the test strip for IFA according to claim 6 in the detection of milk allergens.

15. Use of the test strip for IFA according to claim 7 in the detection of milk allergens.

16. Use of the test strip for IFA according to claim 8 in the detection of milk allergens.

17. The use according to claim 9, wherein the milk allergic components comprise casein, BLG, ALA, lactoferrin and/or BSA.

18. The use according to claim 10, wherein the milk allergic components comprise casein, BLG, ALA, lactoferrin and/or BSA.

19. The use according to claim 11, wherein the milk allergic components comprise casein, BLG, ALA, lactoferrin and/or BSA.

20. The use according to claim 12, wherein the milk allergic components comprise casein, BLG, ALA, lactoferrin and/or BSA.

* * * * *